United States Patent [19]
Butler et al.

[11] Patent Number: 5,506,352
[45] Date of Patent: Apr. 9, 1996

[54] PROCESS FOR THE SYNTHESIS OF 9-(β-D-ARABINOFURANOSYL)ADENINE, 5'-PHOSPHATE

[75] Inventors: Donald E. Butler, Holland, Mich.; Alan Millar, Holly Springs, N.C.

[73] Assignee: Warner-Lambert Company, Morris Plains, N.J.

[21] Appl. No.: 310,360

[22] Filed: Sep. 21, 1994

Related U.S. Application Data

[63] Continuation of Ser. No. 12,106, Feb. 1, 1993, abandoned.

[51] Int. Cl.$^6$ .......................... C07H 19/167; C07H 1/00
[52] U.S. Cl. .................................. 536/55.3; 536/26.13
[58] Field of Search ............................ 536/55.3, 26.13

[56] References Cited

U.S. PATENT DOCUMENTS

| | | | |
|---|---|---|---|
| 3,413,282 | 11/1972 | Yoshikawa et al. | 536/26.1 |
| 3,703,507 | 11/1972 | Haskell et al. | 536/26.1 |
| 3,943,000 | 3/1976 | Ferrar | 127/33 |
| 4,123,609 | 10/1978 | Behnke et al. | 536/26.1 |
| 4,767,873 | 8/1988 | Katz et al. | 556/42 |
| 4,814,407 | 3/1989 | Canova et al. | 528/21 |

*Primary Examiner*—Gary L. Kunz
*Attorney, Agent, or Firm*—Francis J. Tinney

[57] ABSTRACT

An improved process for the preparation of 9-(β-D-arabinofuranosyl)adenine, 5'-phosphate, is described where dried 9-(β-D-arabinofuranosyl)adenine is reacted with triethyl phosphate and phosphorous oxychloride in dichloromethane and the reaction mixture hydrolyzed and excess hydrogen chloride removed with propylene oxide as the acid scavenger. This process gives a yield of about 70–85%, which is nearly double the yields of the prior art.

8 Claims, No Drawings

PROCESS FOR THE SYNTHESIS OF 9-(β-D-ARABINOFURANOSYL)ADENINE, 5'-PHOSPHATE

This is a continuation of Ser. No. 08/012,106 filed Feb. 1, 1993, now abandoned.

BACKGROUND OF THE INVENTION

The present invention relates to an improved process for the production of 9-(β-D-arabinofuranosyl) adenine, 5'-phosphate.

9-(β-D-arabinofuranosyl)adenine, 5'-phosphate, is useful as a medicinal agent, especially as an antiviral agent, being active against Herpes simplex virus as described in U.S. Pat. No. 3,703,507. The compound is also known as Vira-MP® or Vidarabine monophosphate. Since early publication of 9-(β-D-arabinofuranosyl)adenine [Vidarabine, also known as Vira-A®] as an antiviral agent in Adams H. G., et al, *Journal of Infectious Diseases* 1976;133(Suppl):A151–A159, and *Pharmacology & Therapeutics* 1980;8:143–171 by Buchanan R. A. and Hess F., medical interest remains active in Vidarabine and derivatives, for example, a recent study by Whitley R., et al in the *New England Journal of Medicine* 1991;32(7):444–9 comparing Vidarabine and Acyclovir found "In this multicenter, randomized, blinded study there were no differences in outcome between Vidarabine and Acyclovir in the treatment of neonatal herpes simplex virus infection".

U.S. Pat. No. 3,703,507 discloses a process for preparing 9-(β-D-arabinofuranosyl)adenine, 5'-phosphate, by reacting 9-(β-D-arabinofuranosyl) adenine with phosphorus oxychloride in glacial acetic acid in the presence of a tertiary amine base.

U.S. Pat. No. 3,413,282 discloses a process for converting a nucleoside to a 5'-nucleotide phosphate by reaction with phosphorus oxychloride or diphosphoryl chloride (tetrachloropyrophosphate) in the presence of trialkyl phosphate solvent. The reactive product is hydrolyzed, neutralized, and the 5'-nucleotide phosphate isolated by absorption and elution techniques requiring activated carbon or ion exchange resin. The methods disclosed in U.S. Pat. Nos. 3,703,507 and 3,413,282 involve undesirable time-consuming manipulations and processing steps as well as requiring costly separation media and elution solvents.

U.S. Pat. No. 4,123,609 discloses a process for preparing 9-(β-D-arabinofuranosyl)adenine, 5'-phosphate. The process involves reaction of 9-(β-D-arabinofuranosyl)adenine with a phosphorylating agent such as a phosphorus oxyhalide, in particular phosphorus oxychloride, phosphorus oxybromide, and diphosphoryl chloride in the presence of trialkyl phosphate solvent. Subsequently, the reaction mixture is hydrolyzed; the pH of the aqueous hydrolysis mixture is adjusted to the basic side of the pH scale to cause separation into aqueous and nonaqueous liquid phases; the trialkyl phosphate solvent is removed from the aqueous mixture while maintaining the residual aqueous mixture at a pH at which the ester product is insoluble to cause the ester product to precipitate as a solid phase from the aqueous mixture; and isolating the product. Although this process provides the desired 9-(β-D-arabinofuranosyl)adenine, 5'-phosphate, it is difficult to conduct on large-scale. The yields are modest on industrial or large scale, about 55%, and the product formed is a waxy and/or gummy solid that is difficult to isolate and that could not be readily separated from the inorganic salts produced except by ion-exchange chromatography.

The object of the present invention is an improved process for preparing 9-(β-D-arabinofuranosyl)adenine, 5'-phosphate.

The present process is a more specific and scalable process for the production of 9-(β-D-arabinofuranosyl)adenine, 5'-phosphate, and affords higher yields compared to the previous methods.

SUMMARY OF THE INVENTION

Accordingly, a first aspect of the present invention is an improved process for the preparation of 9-(β-D-arabinofuranosyl)adenine, 5'-phosphate:

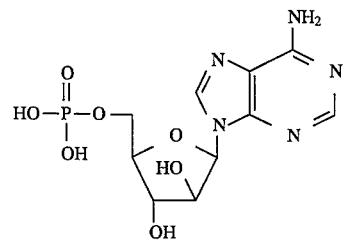

which comprises:

Step (a) drying 9-(β-D-arabinofuranosyl)adenine monohydrate:

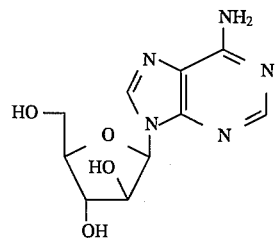

Step (b) adding triethyl phosphate;

Step (c) cooling and adding a solution of phosphorus oxychloride in dichloromethane;

Step (d) hydrolyzing the reaction mixture of Step (c) with water; and

Step (e) separating the formed aqueous and nonaqueous phases and adding the aqueous phase to a solution of propylene oxide in ethanol to afford crystalline 9-(β-D-arabinofuranosyl)adenine, 5'-phosphate.

A second aspect of the present invention is an improved purification procedure for 9-(β-D-arabinofuranosyl)adenine, 5'-phosphate prepared according to the process of the first aspect of the present invention, which comprises:

Step (a) suspending 9-(β-D-arabinofuranosyl) adenine, 5'-phosphate, in water and adjusting the pH to about 6 with 28% aqueous ammonium hydroxide solution;

Step (b) filtering to remove particulate matter;

Step (c) adjusting the pH to about 2.5 with 37% aqueous hydrochloric acid solution; and Step (d) adding anhydrous ethanol to afford crystalline 9-(β-D-arabinofuranosyl)adenine, 5'-phosphate.

DETAILED DESCRIPTION OF THE INVENTION

The process of the present invention is a new, improved, economical, and commercially feasible method for preparing 9-(β-D-arabinofuranosyl)adenine, 5'-phosphate.

Thus, the starting material, 9-(β-D-arabinofuranosyl)adenine monohydrate is dried in vacuo to a water content of ≤0.1% water. The dried nucleoside is mixed with triethyl phosphate and the mixture is cooled with agitation to about −10° C. to about −20° C. Maintaining the temperature at about −20° C. to about 25° C. preferably about −10° C. to about −20° C., a solution of phosphorous oxychloride in dichloromethane at about −10° C. to about 25° C. is added. The kilo amount of phosphorous oxychloride used is calculated by multiplying the kilo amount of anhydrous 9-(β-D-arabinofuranosyl)adenine by a factor of 0.717±5%. The kilo amount of dichloromethane is calculated by multiplying the kilo amount of anhydrous 9-(β-D-arabinofuranosyl)adenine by a factor of 2 to 3. Agitation is continued until an in-process sample indicates less than 3% of unreacted 9-(β-D-arabino-furanosyl)adenine. The in-process sample is treated as follows: 1 mL of the sample is added to 100 mL of water and thoroughly mixed for at least 10 minutes. A 20 μL sample of this is injected onto a high pressure liquid chromatography (HPLC) column.

HPLC Column and Conditions

Column: An Alltech Nucleoside-Nucleotide 7μ, C18, 25 Cm Column

Conditions: 254 nm, 1.00 mL/min using the gradient outlined

Gradient: 0 to 8 minutes hold at 15% solvent B; 8 to 15 minutes increased from 15% to 22% solvent B; 15 to 40 minutes hold at 22% solvent B; 40 to 45 minutes decrease from 22% to 15% solvent B Solvent A: Water 60 mmol $NH_4H_2PO_4$, 5 mmol tetrabutylammonium phosphate Solvent B: Methanol, 5 mmol tetrabutylammonium phosphate The completely phosphorylated mixture is charged to an agitated suspension of ice and water with additional cooling to maintain the temperature of the new mixture between about 0° C. and about 25° C. (about 15° C. to about 20° C. is preferred). After mixing is complete, agitation is continued for about 0.5 hour to about 1.5 hours and the temperature of the mixture is held between about 20° C. and about 25° C. Additional dichloromethane is charged with agitation, agitation is stopped, and the dichloromethane layer is separated. The aqueous layer's temperature is controlled between about 20° C. to about 25° C. An amount of propylene oxide in excess of the hydrogen chloride that could theoretically be produced from total hydrolysis of the phosphorous oxychloride used in the phosphorylation reaction is dissolved in ethanol with vigorous agitation and the temperature adjusted between about 20° C. to about 25° C. The aqueous layer containing the 9-(β-D-arabinofuranosyl)adenine, 5'-phosphate, is added to the propylene oxide solution while holding the temperature at about 20° C. to about 25° C. with cooling. The desired product 9-(β-D-arabinofuranosyl)adenine, 5'-phosphate, crystallizes smoothly from the ethanol/water mixture and can be isolated by filtration or centrifugation. After vacuum drying at about 40° C.±5° C. for about 24 hours to about 48 hours, the material ordinarily meets all specifications and is obtained in high yield.

Additionally, the 9-(β-D-arabinofuranosyl)adenine, 5'-phosphate, from this process may be further purified by suspending the compound in water with agitation at about 20° C. to about 25° C. The pH is adjusted to a pH=6.0±0.1 with 28% aqueous ammonium hydroxide solution and maintaining the reaction temperature below about 25° C. Agitation is continued until essentially complete solution is obtained. The solution is filtered through a 0.45μ filter to remove any haze or particulate matter. The pH of the filtered product mixture is adjusted with 37% aqueous hydrochloric acid solution with agitation while maintaining the temperature between about 20° C. and about 25° C. to a pH=2.5±0.1. To the agitated solution is added a volume of anhydrous ethanol equal to the total volumes of water previously added (water of suspension+water in 28% aqueous ammonium hydroxide solution+water in 37% hydrochloric acid solution) ±5%. Agitation is continued as the 9-(β-D-arabinofuranosyl)adenine, 5'-phosphate, crystallizes and the temperature is held at about 15° C. to about 25° C. for about 24 to about 48 hours. The material is isolated by filtration or centrifugation and is washed with anhydrous ethanol. The 9-(β-D-arabinofuranosyl)adenine, 5'-phosphate, is vacuum dried at about 40° C.±5° C. until a residual solvent assay shows ethanol at ≤1.0% and a Karl Fischer assay indicates ≤7.0% ($H_2O$).

The use of propylene oxide to remove excess hydrogen chloride is crucial to the success of this process. Use of bases used in earlier literature processes such as sodium hydroxide, potassium hydroxide, or ammonium hydroxide results in a product that cannot be readily purified from the resulting sodium chloride without resorting to ion-exchange chromatography.

The use of ethylene oxide, propylene oxide, and butylene oxide as hydrogen chloride scavengers has been reported: (U.S. Pat. Nos. 4,767,873 and 4,814,407 and Canadian Patent 734,021). However, it has been reported that these oxides hydroxyalkylate materials containing OH, NH, and/or $NH_2$ groups. Basic catalysts have been used to accelerate the rate of reaction and to obtain high yields but are not required for reaction to occur. (Great Britain Patent Numbers 1,082,673A and 1,504,432A; Japanese Patent 89,013,484B; and German Published Patent Application DD 219,204).

Thus, we surprisingly and unexpectedly found that propylene oxide could be used as a scavenger for hydrogen chloride in the preparation of a compound containing polyhydroxyl and amine functionalities, namely 9-(β-D-arabinofuranosyl)adenine, 5'-phosphate, without the formation of undesirable by-products resulting from hydroxypropylation by propylene oxide.

EXAMPLE 1

9-(β-D-Arabinofuranosyl)adenine, 5'-phosphate 9-(β-D-arabinofuranosyl)adenine, Monohydrate (2.5 Kg), is dried in a vacuum tray drier at 90° C.±5° C. and 26 to 28 inches of Hg, until a Karl Fischer analysis indicates ≤0.1% water. The following calculation is performed to calculate the needed amount of phosphorous oxychloride ($POCl_3$):

2.4 Kg (net weight) of 9-(β-D-arabinofuranosyl) adenine× 0.717=1.72 Kg of $POCl_3$ The 9-(β-D-arabinofuranosyl)adenine is charged to a 20 gallon glass-lined still. Triethyl phosphate (47 Kg) is charged to the same still and a nitrogen ($N_2$) blanket of 5 lbs per square inch (psig) is applied to the sealed still (used to exclude atmospheric moisture while cooling the contents). The mixture is agitated and cooled to between −15° C. and −20° C. The number of kilograms of $POCl_3$ as calculated= 1.72 Kg is mixed under $N_2$ with 6.5 Kg of dichloromethane ($CH_2Cl_2$). The $POCl_3/CH_2Cl_2$ solution is (may be precooled to −15° C. to −100° C.) cooled to −15° C. to −0° C. and pumped into the inerted 20 gallon still at a flow rate of 50±10 mL per minute maintaining the temperature of the reaction mixture between −15° C. and −20° C. with cooling. The last of the $POCl_3/CH_2Cl_2$ solution is rinsed into the reactor with 0.5 Kg of dichloromethane. Agitation is continued until an in-process sample indicates less than 3% unreacted 9-(β-D-arabinofuranosyl) adenine. The in-process sample is treated as follows: 1 mL of the sample is added to 100 mL of water and thoroughly mixed for at least 10 minutes. A 20 μL sample of this is injected onto the HPLC column.

HPLC Column and Conditions

Column: An Alltech Nucleoside-Nucleotide 7μ, C18, 25 Cm Column

Conditions: 254 nm, 1.00 mL/min using the gradient outlined

Gradient: 0 to 8 minutes hold at 15% solvent B; 8 to 15 minutes increased from 15% to 22% solvent B; 15 to 40 minutes hold at 22% solvent B; 40 to 45 minutes decrease from 22% to 15% solvent B Solvent A: Water 60 mmol $NH_4H_2PO_4$, 5 mmol tetrabutylammonium phosphate Solvent B: Methanol, 5 mmol tetrabutylammonium phosphate When the in-process assays show less than 3.0% of 9-(β-D-arabinofuranosyl)adenine, the mixture is poured into an agitated mixture of 16 Kg of demineralized water and 16 Kg of ice with cooling to maintain the temperature at 15° C.±2° C. The mixture is allowed to warm to 20° C. to 25° C. when the addition is complete and agitated for 45 to 60 minutes. Dichloromethane (53 Kg) is then added and the mixture agitated vigorously for 30 minutes. The agitator is turned off, the layers are allowed to separate for 30 minutes, and the dichloromethane layer is drained. Another addition of dichloromethane, 13.8 Kg, is made. The mixture is agitated vigorously for 30 minutes, the layers are allowed to separate, and the dichloromethane layer is drained. The aqueous layer is filtered through a 0.45μ filter to remove any particulates and the filter is washed with 2 L of demineralized water that is added to the filtrate. In a 50 gallon glass-lined reactor, propylene oxide (2.3 Kg) and 103 Kg of anhydrous 2B ethanol are charged, agitated vigorously, and the temperature of the mixture held at 20° C. to 25° C. The aqueous product solution from the 20 gallon glass-lined still is pumped through an 0.45μ filter into the propylene oxide/ethanol solution with vigorous agitation while holding the temperature between 20° C. to 25° C. The time consumed is approximately 50 minutes at this scale in this equipment. The agitation is continued as the product crystallizes over a 24-hour period. The 9-(β-D-arabinofuranosyl)adenine, 5'-phosphate, is isolated on a centrifuge and washed with 20 Kg of anhydrous 2B ethanol. The crystalline solid is spun as dry as is reasonable on the centrifuge, transferred to poly-lined trays, and dried in a vacuum tray drier at 40° C.±5° C. and 26 to 28 inches of Hg vacuum, until analysis of a sample by Karl Fischer indicates less than 7.0% $H_2O$ and analysis shows that residual solvent, ethanol, is below 1.0%. The yield is 2.95 Kg, 98% of 9-(β-D-arabinofuranosyl) adenine, 5'-phosphate, with good purity. (Assay vs Vidarabine= 83.73% wt/wt; assay vs a reference standard of 9-(β-D-arabinofuranosyl)adenine, 5'-phosphate=85.24% wt/wt.)

If greater purity is needed, 9-(β-D-arabinofuranosyl)adenine, 5'-phosphate, made by the previous process can be further purified as follows:

9-(β-D-arabinofuranosyl)adenine, 5'-phosphate, 2.5 Kg is charged to an inerted 50 gallon glass-lined still followed by 30 Kg of demineralized water. The agitator is started and the temperature of the slurry is adjusted to between 20° C. and 25° C. Ammonium hydroxide, 28% solution, is added until the pH of the mixture is 6.0±0.1 maintaining the temperature below 25° C. The agitation is continued until solution is essentially complete. The solution is filtered through a 0.45μ filter, followed by a rinse with 5 Kg of demineralized water.

While maintaining the temperature of the mixture between 20° C. and 25° C. with cooling, the pH of the aqueous product mixture is adjusted to 2.5±0.1 using filtered 37% aqueous hydrochloric acid solution. At a rate of 0.5 to 1 L/minute, charge 28 Kg of filtered anhydrous 2B ethanol to the stirring aqueous product mixture. As crystallization occurs, agitation is continued and the temperature is held between 15° C. and 25° C. for 24 to 48 hours. The crystalline product is isolated by centrifugation and the product is washed with 20 Kg of anhydrous 2B ethanol. The crystalline solid is spun as dry as is reasonable on the centrifuge, transferred to poly-lined trays, and dried in a vacuum tray drier at 40° C.±5° C. and 26 to 28 inches of Hg vacuum until analyses by Karl Fischer shows less than 7% water and residual solvent analysis shows less than 1.0% ethanol. The yield is 1.76 Kg (70%) of highly pure 9-(β-D-arabinofuranosyl)adenine, 5'-phosphate. (Assay vs Vidarabine=88.38% wt/wt uncorrected for solvent, assay vs reference standard of product=94.81% wt/wt.)

We claim:

1. A process for preparing 9-(β-D-arabinofuranosyl) adenine-5'-phosphate:

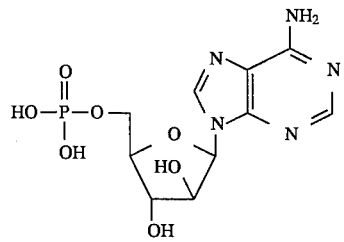

which comprises:

Step (a): drying 9-(β-D-arabinofuranosyl)adenine monohydrate until the water content is less than or equal to 0.1%;

Step(b): adding triethyl phosphate to the the dry 9-(β-D-arabinofuranosyl)adenine monohydrate;

Step(c): cooling the above mixture to about −10° C. to about −20° C. and adding a solution of phosphorus oxychloride in dichloromethane at about −10° C. to about 25° C. wherein the amount of phosphorus oxychloride used is 0.681–0.753 times the mass of 9-(β-D-arabinofuranosyl)adenine; the amount of dichloromethane used is 2 to 3 times the mass of 9-(β-D-arabinofuranosyl)adenine;

Step(d): hydrolyzing the reaction mixture of Step(c) with a mixture of 50% ice and water at about 0° C. to about 25° C., followed by the addition of dichloromethane;

Step(e): separating the formed aqueous and nonaqueous phases and adding the aqueous phase to a solution of propylene oxide in ethanol wherein the amount of propylene oxide is in excess over the amount of theoretical hydrogen chloride produced from the hydroylsis of phosphorus oxychloride; and Step(f): isolating the crystalline 9-(β-D-arabinofuranosyl)adenine- 5'-phosphate by filtration or centrifugation.

2. The process of claim 1 wherein the solution of phosphorus oxychloride in dichloromethane is added at about −15° C. to about −20° C.

3. The process of claim 1 wherein the hydrolysis Step(d) is carried out at about 15° C.±2° C. and the mixture is allowed to warm to about 20° C. to about 25° C.

4. The process of claim 1 wherein the 9-(β-D-arabinofuranosyl)adenine- 5'-phosphate is isolated by centrifugation.

5. The process of claim 1 which further comprises for additional purification the following steps:

1) suspending the 9-(β-D-arabinofuranosyl)adenine-5'-phosphate of Step(f) in water;
2) adjusting the pH to about 6 with 28% aqueous ammnonium hydroxide;
3) filtering to remove particulate matter;
4) adjusting the pH to about 2.5 with 37% aqueous hydrochloric acid solution; and
5) adding anhydrous ethanol to afford crystalline 9-(β-D-arabinofuranosyl)adenine-5'-phosphate.

6. The process of claim 5 wherein the solution is filtered through a 0.45 micron filter.

7. The process of claim 5 wherein the crystalline 9-(β-D-arabinofuranosyl)adenine-5'-phosphate is isolated by filtration or centrifugation.

8. The process of claim 5 wherein the crystalline 9-(β-D-arabinofuranosyl)adenine-5'-phosphate is isolated by centrifugation.

* * * * *